United States Patent
Yamashita et al.

(10) Patent No.: US 10,022,518 B2
(45) Date of Patent: Jul. 17, 2018

(54) MEDICAL TUBE AND CATHETER

(71) Applicant: TERUMO KABUSHIKI KAISHA, Shibuya-ku (JP)

(72) Inventors: Yasunori Yamashita, Shizuoka (JP); Tooru Oota, Shizuoka (JP); Youichi Ito, Shizuoka (JP); Naoko Katou, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 960 days.

(21) Appl. No.: 14/283,253

(22) Filed: May 21, 2014

(65) Prior Publication Data
US 2014/0257111 A1  Sep. 11, 2014

Related U.S. Application Data

(63) Continuation of application No. PCT/JP2012/079841, filed on Nov. 16, 2012.

(30) Foreign Application Priority Data

Nov. 25, 2011 (JP) ................................ 2011-258163

(51) Int. Cl.
*A61M 25/00* (2006.01)
*A61B 1/00* (2006.01)
(Continued)

(52) U.S. Cl.
CPC .......... *A61M 25/0043* (2013.01); *A61B 1/005* (2013.01); *A61B 1/00064* (2013.01);
(Continued)

(58) Field of Classification Search
CPC .......... A61M 25/0043; A61M 25/0023; A61M 25/0054; A61M 25/0009; A61M 25/0141;
(Continued)

(56) References Cited

U.S. PATENT DOCUMENTS 5,533,985 A * 7/1996 Wang ................ A61M 25/0009
600/433
6,007,478 A * 12/1999 Siess ................ A61M 25/0053
600/16
(Continued)

FOREIGN PATENT DOCUMENTS

CN 101001658 A 7/2007
CN 101933821 A 1/2011
(Continued)

OTHER PUBLICATIONS

Polymer by Wikipedia; pub. online on Nov. 7, 2011 at https://en.wikipedia.org/w/index.php?title=Polymer&oldid=459498293.*
(Continued)

*Primary Examiner* — Katherine Fernandez
*Assistant Examiner* — Michael Kellogg
(74) *Attorney, Agent, or Firm* — Buchanan Ingersoll & Rooney PC

(57) ABSTRACT

A medical tube includes a first portion, a second portion, a third portion, and a fourth portion in this order from a proximal side to a distal side thereof. The first portion has a tubular resin layer, the second portion has a tubular inner layer and outer layer, the third portion as an inner layer and outer layer, and the fourth portion has a tubular resin layer. When flexural rigidity of the first portion, the second portion, the third portion, and the fourth portion is G1, G2, G3, and G4, respectively, the flexural rigidity of each portion being configured to have a relationship with each other portion based upon the following expression (1):

$$G1 > G2 > G3 > G4 \qquad (1).$$

17 Claims, 4 Drawing Sheets

(51) Int. Cl.
*A61B 1/005* (2006.01)
*A61M 25/01* (2006.01)
*A61B 8/12* (2006.01)

(52) U.S. Cl.
CPC ..... *A61B 1/00078* (2013.01); *A61M 25/0009* (2013.01); *A61M 25/0023* (2013.01); *A61M 25/0054* (2013.01); *A61B 8/12* (2013.01); *A61M 25/0053* (2013.01); *A61M 25/0141* (2013.01); *A61M 2025/0183* (2013.01)

(58) Field of Classification Search
CPC .. A61B 1/00078; A61B 1/005; A61B 1/00064
See application file for complete search history.

(56) References Cited

U.S. PATENT DOCUMENTS

| | | |
|---|---|---|
| 2002/0022825 A1 | 2/2002 | Saitou et al. |
| 2003/0195419 A1 | 10/2003 | Harada |
| 2006/0229589 A1 | 10/2006 | Itou et al. |
| 2007/0100285 A1 | 5/2007 | Griffin et al. |
| 2008/0188832 A1 | 8/2008 | Tanioka et al. |
| 2008/0262472 A1 | 10/2008 | Lunn et al. |
| 2011/0082443 A1 | 4/2011 | Griffin et al. |

FOREIGN PATENT DOCUMENTS

| | | | |
|---|---|---|---|
| EP | 1787674 A1 * | 5/2007 | ............ A61M 25/00 |
| EP | 2 213 325 A1 | 8/2010 | |
| JP | 9-512445 A | 12/1997 | |
| JP | 11-239617 A | 9/1999 | |
| JP | 2006-288670 A | 10/2006 | |
| JP | 3954888 B2 | 8/2007 | |
| JP | 2008-188304 A | 8/2008 | |
| JP | 2011-083594 A | 4/2011 | |
| WO | 95/28982 A1 | 11/1995 | |
| WO | WO 2009/054509 A1 | 4/2009 | |

OTHER PUBLICATIONS

Adhesive by Wikipedia; pub. online on Oct. 25, 2011 at https://en.wikipedia.org/w/index.php?title=Adhesive&oldid=457310440.*
Polyethylene by Wikipedia; pub. online on Nov. 8, 2011 at https://en.wikipedia.org/w/index.php?title=Polyethylene&oldid=459593603.*
Polyether ether ketone by Wikipedia; pub. online on Sep. 19, 2011 at https://en.wikipedia.org/w/index.php$8 title=Polyether_ether_ketone&oldid=451409245.*
Office Action dated Sep. 14, 2015, by the Chinese Patent Office in corresponding Chinese Patent Application No. 201280056812.7 (8 pgs).
Office Action (Notification of Reasons for Refusal) dated Sep. 27, 2016, by the Japanese Patent Office in corresponding Japanese Patent Application No. 2013-545908. (4 pages).
International Search Report (PCT/ISA/210) dated Feb. 19, 2013, by the Japanese Patent Office as the International Searching Authority for International Application No. PCT/JP2012/079841.

* cited by examiner

MEDICAL TUBE AND CATHETER

CROSS REFERENCES TO RELATED APPLICATIONS

This application is a continuation application of International Application No. PCT/JP2012/079841 filed on Nov. 16, 2012, and claims priority to Japanese Application No. 2011-258163 filed on Nov. 25, 2011, the entire content of both of which is incorporated herein by reference.

TECHNICAL FIELD

The disclosure here relates to a medical tube and a catheter.

BACKGROUND DISCUSSION

There is known a catheter employed to be inserted into a biological lumen such as a blood vessel and to diagnose the inside of the biological lumen by ultrasonic waves (for example, refer to Japanese Patent No. 3954888).

Japanese Patent No. 3954888 discloses a catheter including a catheter main body that has a lumen, and a shaft that is inserted into the lumen of the catheter main body and has an ultrasonic wave oscillation portion emitting the ultrasonic waves at a distal portion. The catheter rotates the shaft inserted into the lumen of the catheter main body around an axis of the shaft and moves the shaft in a proximal direction, and thus, it is possible to acquire an ultrasonic wave image of a vascular wall.

In such a catheter, in order to improve operability and prevent kinks, as a medical tube employed for the catheter main body, a tube of which rigidity is gradually decreased from its intermediate portion toward a distal side is required.

SUMMARY

An exemplary embodiment of the disclosure herein provides a medical tube and a catheter of which rigidity is gradually decreased from an intermediate portion toward a distal side of the tube.

According to one aspect of the disclosure, a resin medical tube is provided including a first portion; a second portion; a third portion; and a fourth portion, in this order from a proximal side toward a distal side.

The first portion has a tubular resin layer.

The second portion has a tubular inner layer and a tubular outer layer that is provided on an outer periphery side of the inner layer.

The third portion has a tubular inner layer and a tubular outer layer that is provided on an outer periphery side of the inner layer.

The fourth portion has a tubular resin layer.

When the rigidity of the first portion is G1, the rigidity of the second portion is G2, the rigidity of the third portion is G3, and the rigidity of the fourth portion is G4, the rigidity of each portion has a relationship with each other portion based upon the following expression (1):

$$G1 > G2 > G3 > G4 \tag{1}$$

In the medical tube according to an exemplary embodiment of the disclosure, it is preferable that the resin layer of the first portion and the inner layer of the second portion be integrally formed of the same material.

In the medical tube according to an exemplary embodiment of the disclosure, it is preferable that the outer layer of the second portion and the outer layer of the third portion be integrally formed of the same material.

In the medical tube according to the present invention, it is preferable that the inner layer of the third portion and the resin layer of the fourth portion be integrally formed of the same material.

In the medical tube according to an exemplary embodiment of the disclosure, it is preferable that a thickness of the inner layer of the second portion be thinner than a thickness of the resin layer of the first portion.

In the medical tube according to an exemplary embodiment of the disclosure, it is further preferred that the rigidity of a configuration material of the outer layer of the second portion be less than the rigidity of the configuration material of the resin layer of the first portion.

It is also preferable that the rigidity of the material of the inner layer of the third portion be less than the rigidity of the material of the inner layer of the second portion.

It is further preferred that the rigidity of the material of the inner layer of the third portion be less than the rigidity of the material of the outer layer of the second portion.

In the medical tube according to an exemplary embodiment of the disclosure, it is preferable that the material of the resin layer of the first portion contain polyether ether ketone.

It is further preferred that the material of the outer layer of the second portion contain a polyolefin.

In the medical tube according to an exemplary embodiment of the disclosure, it is preferable that the material of the inner layer of the third portion contain the polyolefin.

More particularly, in the medical tube according to an exemplary embodiment of the disclosure, it is preferable that the material of the outer layer of the second portion contain the polyolefin, and the material of the inner layer of the third portion contain the polyolefin of which a molecular weight is less than that of the polyolefin of the material of the outer layer of the second portion.

It is preferable that an inner diameter of the first portion, an inner diameter of the second portion, an inner diameter of the third portion, and an inner diameter of the fourth portion be substantially the same as each other.

In the medical tube according to an exemplary embodiment of the disclosure, it is also preferable that an outer diameter of the fourth portion be the smallest among an outer diameter of the first portion, an outer diameter of the second portion, an outer diameter of the third portion, and the outer diameter of the fourth portion.

Further, it is preferred that the outer diameter of the first portion and the outer diameter of the second portion be substantially the same as each other.

In the medical tube according to an exemplary embodiment of the disclosure, it is preferable to include a first adhesive agent which is provided in a bonding portion between the resin layer of the first portion and the outer layer of the second portion; and a second adhesive agent which is provided in the vicinity of the bonding portion between the inner layer of the second portion and the outer layer of the second portion.

It is also preferable that the first adhesive agent have resistance to chemicals.

In the medical tube according to an exemplary embodiment of the disclosure, it is preferable to include a fifth portion that is provided between the second portion and the third portion.

In the medical tube according to an exemplary embodiment of the disclosure, it is preferable that the medical tube be inserted into a biological lumen to be used, and is employed for a catheter main body of a catheter which includes the catheter main body having flexibility.

According to another aspect of the disclosure, a catheter is provided configured to be inserted into a biological lumen for use and including a catheter main body having a flexibility characterized in that the catheter main body includes the medical tube according to the exemplary embodiment of the disclosure.

In the catheter according to the present invention, it is preferable that a lumen of the medical tube be employed as a sensor lumen in which a drive shaft that has an image-capturing portion on its distal portion capturing an image inside the biological lumen is inserted.

In the catheter according to an exemplary embodiment of the disclosure, it is preferable that the catheter main body be arranged in parallel to the sensor lumen and have a guide wire lumen in which a guide wire is inserted.

According to the disclosure, it is possible to provide a medical tube of which rigidity is gradually decreased from an intermediate portion toward a distal side of the tube.

Particularly, when the medical tube according to the disclosure is employed for a catheter main body of a catheter, it is possible to improve operability thereof and prevent kinks.

DETAILED DESCRIPTION

Hereinafter, a medical tube and a catheter according to the disclosure here will be described in detail based on a suitable embodiment illustrated in the accompanying drawings. Note that, usage of the medical tube according to the disclosure is not particularly limited, and in the embodiment below, representatively, a case will be described in which the medical tube according to the disclosure is applied to a member of the catheter, that is, a drive shaft insertion portion configuring a portion of a catheter main body.

Figure 1:
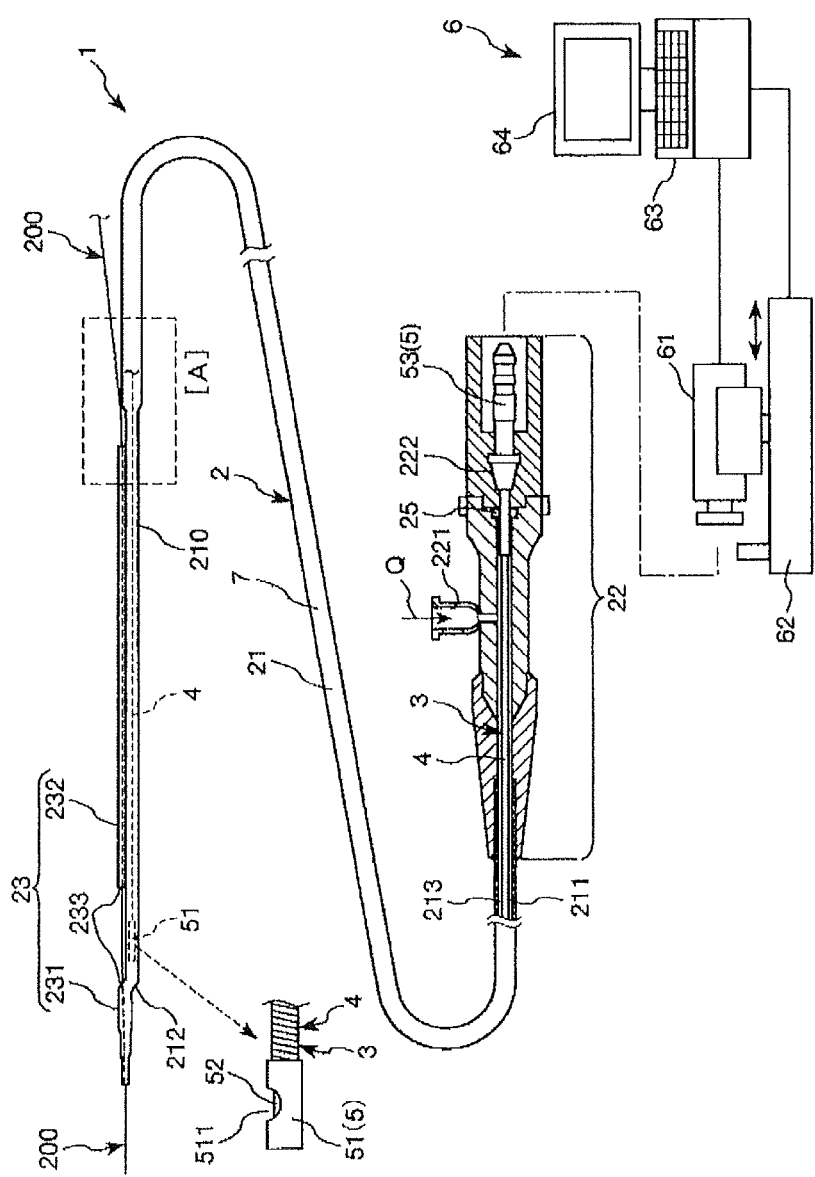
FIG. 1 is a partial longitudinal-section side view illustrating an embodiment of a catheter assembly including a catheter according to an exemplary embodiment of the disclosure.
Figure 2:
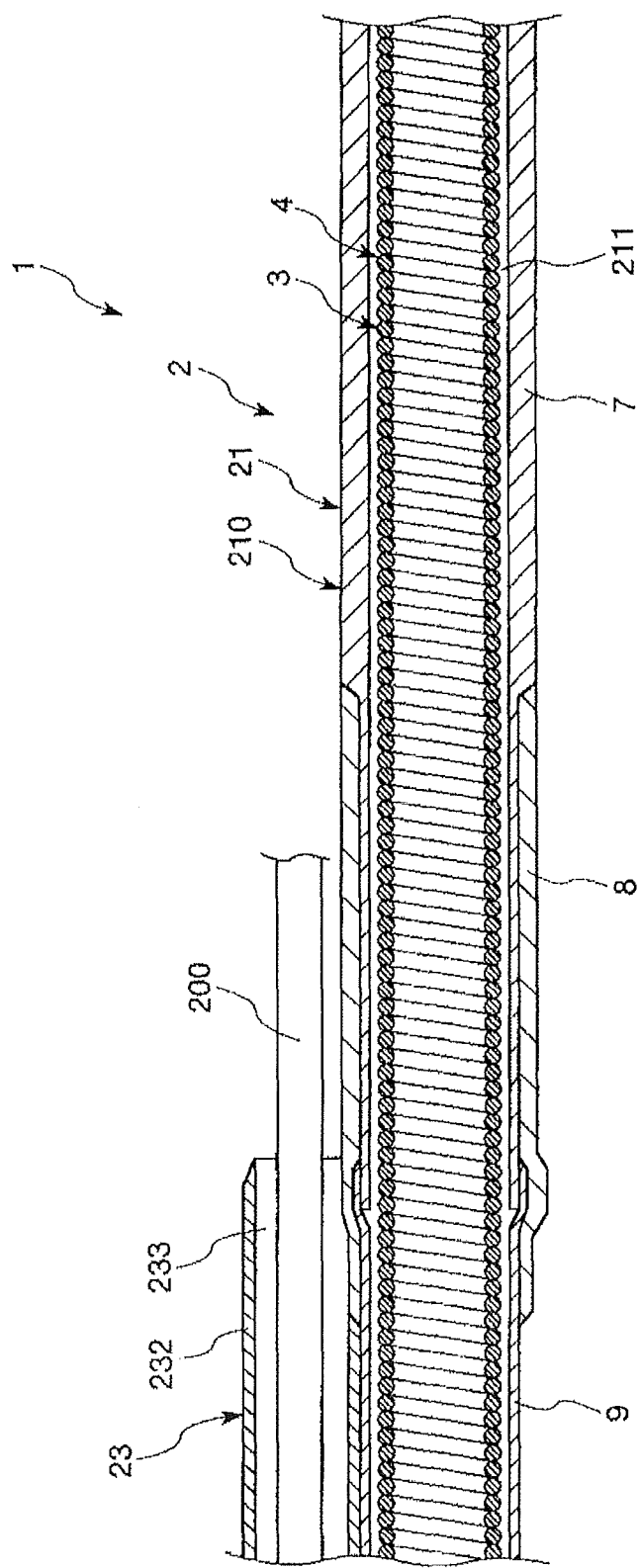
FIG. 2 is an enlarged longitudinal sectional view of a region [A] surrounded by the dotted line in FIG. 1.
Figure 3:
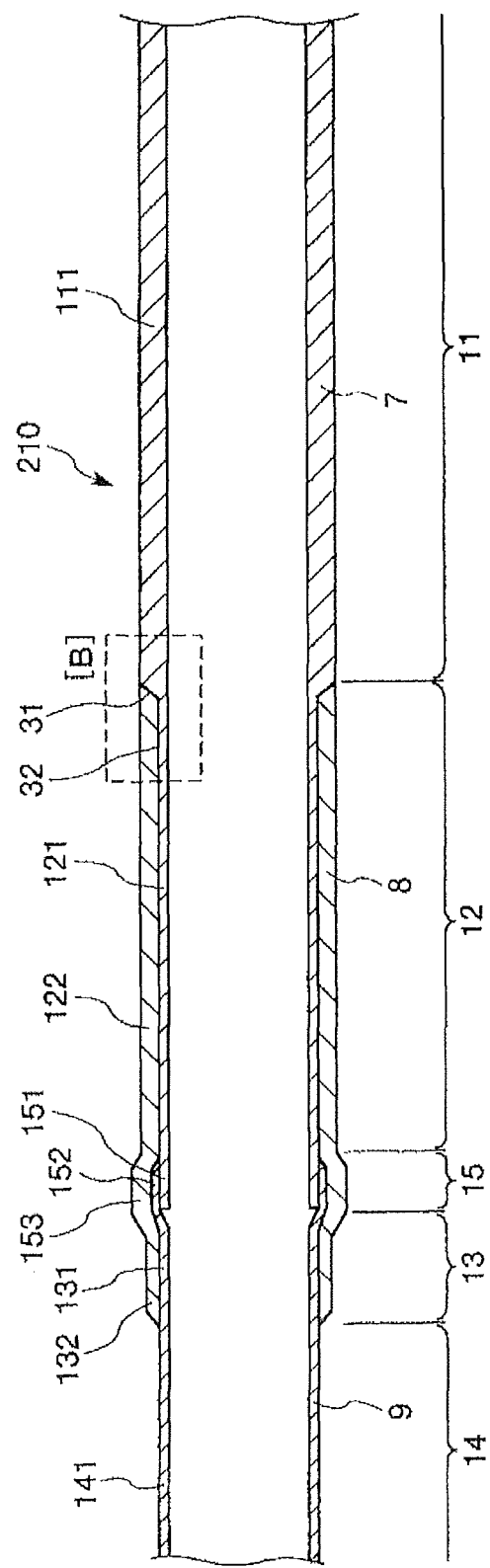
FIG. 3 is a longitudinal sectional view illustrating an embodiment of a drive shaft insertion portion in a state before a guide wire insertion through portion is disposed in the catheter assembly illustrated in FIG. 1, that is, a medical tube according to an exemplary embodiment of the disclosure.
Figure 4:
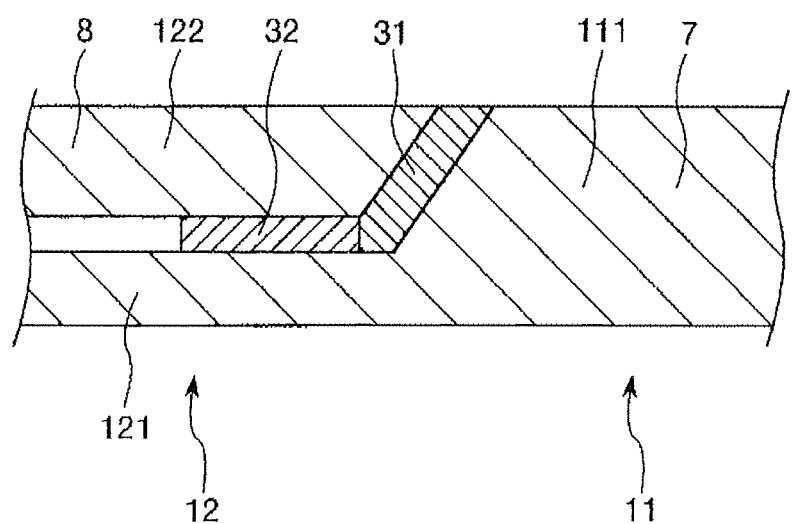
FIG. 4 is an enlarged longitudinal sectional view of a region [B] surrounded by the dotted line in FIG. 3.

FIG. 1 is a partial longitudinal-section side view illustrating an embodiment of a catheter assembly including the catheter according to the disclosure. FIG. 2 is an enlarged longitudinal sectional view of a region [A] surrounded by the dotted line in FIG. 1. FIG. 3 is a longitudinal sectional view illustrating an embodiment of the drive shaft insertion portion in a state before a guide wire insertion through portion is disposed in the catheter assembly illustrated in FIG. 1, that is, the medical tube according to an exemplary embodiment of the disclosure. FIG. 4 is an enlarged longitudinal sectional view of a region [B] surrounded by the dotted line in FIG. 3. FIG. 3 corresponds to FIG. 2 and illustrates a portion corresponding to the region [A] surrounded by the dotted line in FIG. 1.

Hereinafter, the left side in FIGS. 1 to 4 is considered to be "distal", the right side is "proximal", the upper side is "above", and the lower side is "below" in the description.

A catheter assembly 1 illustrated in FIGS. 1 and 2 includes a catheter 2 and a drive shaft 3 which is inserted into the catheter 2. The catheter assembly 1 is inserted into a biological lumen (representatively regarded hereinafter as a "blood vessel") to be employed and acquires an image of a vascular wall which is an inner image thereof in an assembled state where the catheter 2 and the drive shaft 3 are assembled.

In addition, the catheter assembly 1 can be connected to an external unit 6. The external unit 6 is formed of a scanner apparatus 61 in which an external driving source such as a motor is built, an axial direction movement apparatus 62 which grasps and moves the scanner apparatus 61 in a horizontal direction (axial direction) using the motor and the like, a control portion 63 which functions to control an operation of the scanner apparatus 61 and the axial direction movement apparatus 62, and a display portion 64 which displays the image of the vascular wall obtained by the catheter assembly 1.

Before describing each portion of the catheter assembly 1, the external unit 6 will be described.

A proximal portion of the catheter assembly 1 is connected to the scanner apparatus 61. The scanner apparatus 61 can rotate the drive shaft 3 around its axis, and the entire catheter assembly 1 is movable along an axial direction thereof by the axial direction movement apparatus 62. Accordingly, it is possible to perform scanning using an ultrasonic oscillator (image-capturing portion) 52 of the drive shaft 3. In addition, it is possible to form an image of the vascular wall based on information which can be obtained from reflected waves of the ultrasonic oscillator 52 of the drive shaft 3 using a scanner built into the scanner apparatus 61. Accordingly, in an arbitrary position with respect to the blood vessel, throughout the overall periphery in a circumferential direction thereof, it is possible to obtain a transverse sectional image inside the blood vessel which is an ultrasonic image.

The control portion 63 is, for example, a personal computer in which a central processing unit (CPU) is built.

The display portion 64 is, for example, a liquid crystal display apparatus.

As aforementioned, the catheter assembly 1 includes the catheter 2 and the drive shaft 3. The catheter 2 includes an elongated catheter main body 21 having flexibility, and a connector portion 22 fixed to a proximal portion of the catheter main body 21.

In the catheter main body 21, a sensor lumen 211, in which the drive shaft 3 is inserted, and a guide wire lumen 233, in which a guide wire 200 is inserted, are formed along a longitudinal direction of the catheter main body 21. In addition, a distal portion of the catheter main body 21 includes a reduced diameter portion in which an outer diameter is reduced.

The sensor lumen 211 allows the drive shaft 3 to be inserted therein and is formed along the overall length of the catheter main body 21. Note that, a portion where the sensor lumen 211 is provided in the catheter main body 21 defines a drive shaft insertion portion 210 allowing the drive shaft 3 to be inserted therein. The drive shaft insertion portion 210 will be described in detail later.

In addition, the guide wire lumen 233 allows the guide wire 200 to be inserted therethrough, and in the exemplary embodiment as shown, is formed only in the distal portion of the catheter main body 21. Further, a portion where the guide wire lumen 233 is provided in the catheter main body 21 defines a guide wire insertion through portion 23 allowing the guide wire 200 to be inserted therethrough.

In a state where the drive shaft 3 is inserted, that is, in an insertion state, a liquid Q fills the inside of the sensor lumen 211. An ultrasonic wave from the ultrasonic oscillator 52 can be transmitted to the vascular wall and can return again to the ultrasonic oscillator 52 from the vascular wall by filling the liquid Q. Accordingly, it is possible to reliably acquire the ultrasonic image. The liquid Q, without being particularly limited, can be, for example, a physiological salt solution, a contrast medium and the like.

In addition, the sensor lumen 211 has an opening portion 212 which is open at a distal end of the catheter main body 21. The liquid Q filling the sensor lumen 211 is discharged through the opening portion 212. Accordingly, even if the liquid Q excessively fills the sensor lumen 211, it is possible to reliably prevent damage to the catheter main body 21 caused by the excessive filling.

Although the opening portion 212 is open toward an inclined direction with respect to a central axis of the catheter main body 21 in the configuration illustrated in FIG. 1, without being limited thereto, for example, the opening portion 212 may be open toward a central axial direction of the catheter main body 21, that is, a distal direction.

The catheter main body 21 includes the guide wire insertion through portion 23 allowing the guide wire 200 to be inserted therethrough. The guide wire insertion through portion 23 is configured to have two insertion through members 231 and 232 formed in tubular shapes of which both ends are respectively open. Each of the insertion through members 231 and 232 are disposed to be away from each other along the longitudinal direction of the catheter main body 21. The guide wire lumen 233 thus defines a lumen of the guide wire insertion through portion 23, and the guide wire lumen 233 is arranged in parallel to the sensor lumen 211. The catheter 2 is inserted into the blood vessel such that the guide wire 200 is inserted through the guide wire lumen 233 of the guide wire insertion through portion 23. Hence, the guide wire 200 can be promptly taken out and put into the catheter 2, that is, the catheter is preferably a so-called "rapid exchange type (short monorail type)".

Although the guide wire insertion through portion 23 is preferably disposed parallel to the central axis of the catheter main body 21 in the configuration illustrated in FIG. 1, without being limited thereto, for example, the guide wire insertion through portion 23 may also be disposed at an incline with respect to the central axis of the catheter main body 21.

In addition, in an intermediate portion of the insertion through member 231 on a distal side of the guide wire insertion through portion 23 in the longitudinal direction, a coil (not illustrated) is embedded. The coil functions as an imaging marker to visually recognize a position of a distal portion of the catheter 2 during X-ray irradiation. Preferably, the coil is constructed from a metal material such as platinum, for example, having an X-ray impermeable property.

The catheter main body 21 is made from a material having flexibility, such as, without being particularly limited, for example, thermoplastic resins such as a polyolefin such as a polyethylene and a polypropylene; a polyvinyl chloride; a polyvinylidene chloride; a polyurethane; a polyvinylidene fluoride; a halogenated polyolefin; a polyethylene terephthalate; a polybutylene terephthalate; a polycarbonate; a polyether ether ketone; a silicone rubber; and various thermoplastic elastomers such as a styrene-based elastomer, a polyolefin-based elastomer, a polyurethane-based elastomer, a polyester-based elastomer, a polyamide-based elastomer, a polyimide-based elastomer, a polybutadiene-based elastomer, a trans polyisoprene-based elastomer, a fluororubber-based elastomer, a chlorinated polyethylene-based elastomer, and the like, and it is possible to employ one type or a combination of more than two types (polymer alloys, polymer blends, laminates, and the like) thereamong.

In addition, a tube wall of the catheter main body 21 may be a single layer or it may be a laminate in which a plurality of layers are laminated.

The connector portion 22 fixed to the proximal portion of the catheter main body 21 is defined by a hard tubular body. The connector portion 22 is connected to the scanner apparatus 61 of the external unit 6.

Note that, a method of fixing the connector portion 22 with respect to the catheter main body 21, without being particularly limited, for example, may include a method of adhesion (adhesion using adhesive agent or solvent), a method of fusion (heat fusion, high-frequency fusion, ultrasonic fusion, and the like), and the like can be exemplified.

In an intermediate portion of the connector portion 22 in the longitudinal direction, a liquid injection port 221 branches from the connector portion 22 and is formed in a projected manner. It is possible to inject the liquid Q from the liquid injection port 221 employing a syringe. Then, the injected liquid Q fills the sensor lumen 211 of the catheter main body 21.

In the proximal portion of the connector portion 22, there is provided a rotary movement support portion 222 rotatably supporting the drive shaft 3.

In addition, in the proximal portion of the connector portion 22, a seal member 25 is installed to be closer to a distal side than the rotary movement support portion 222. The seal member 25 is defined by an elastic body formed in a ring shape. Accordingly, the seal member 25 can prevent a gap from occurring between an inner periphery portion of the connector portion 22 and an outer periphery portion of the drive shaft 3, that is, a liquid-tight environment can be maintained, and thus, it is possible to prevent the liquid Q from leaking toward the proximal direction.

The connector portion 22, without being particularly limited, is preferably made from, for example, various resins can be exemplified such as a polyvinyl chloride, a polyethylene, a polypropylene, a cyclic polyolefin, a polystyrene, a poly(4-methylpentene-1), a polycarbonate, an acrylic resin, an acrylonitrile-butadiene-styrene copolymer, a polyethylene terephthalate, a polyester such as a polyethylene naphthalate, a butadiene-styrene copolymer, a polyamide (for example, nylon 6, nylon 6.6, nylon 6.10, nylon 12).

Although the connector portion 22 is a portion in which three tubular bodies are interlocked along the longitudinal direction in the configuration illustrated in FIG. 1, without being limited thereto, for example, the connector portion 22 may be formed with only one tubular body or two or more tubular bodies.

The drive shaft 3 is inserted in the sensor lumen 211 of the catheter main body 21 of the catheter 2. Then, the drive shaft 3 in the insertion state rotates around its central axis by an operation of the scanner apparatus 61.

The drive shaft 3 has an elongated shaft 4 which forms its main body, a housing 51 fixed to a distal portion of the shaft 4, the ultrasonic oscillator 52 accommodated inside the housing 51, and a connector portion 53 fixed to a proximal portion of the shaft 4. In addition, in the drive shaft 3, the housing 51, the ultrasonic oscillator 52, and the connector portion 53 defines an imaging means 5 which captures an image of the vascular wall.

The shaft 4 has torque transmissibility which can reliably transmit a rotating force to the ultrasonic oscillator 52 by the operation of the scanner apparatus 61. The shaft 4 is formed, for example, by tight-winding a metal wire such as stainless steel in a coil shape (refer to FIG. 2). Note that, the metal wire may be wound in a multiplex manner.

An outer diameter of the shaft 4 is smaller than a diameter of the sensor lumen 211. Accordingly, a gap 213 is formed between an outer peripheral surface of the shaft 4 and an inner peripheral surface of the catheter main body 21. The liquid Q injected from the liquid injection port 221 of the catheter 2 flows down the gap 213 and is discharged from the opening portion 212.

In the distal portion of the shaft 4, the housing 51 is fixed, for example, by the adhesive agent. The housing 51 is made from a metal cylindrical body such as stainless steel, and a through hole 511 passing through a wall portion thereof is formed therein. The ultrasonic oscillator 52 is exposed from the through hole 511. Note that, a diameter of the housing 51 is substantially the same as the outer diameter of the shaft 4 or slightly larger.

The ultrasonic oscillator 52 is fixed inside the housing 51 such that its center is positioned on the central axis of the shaft 4. Accordingly, the ultrasonic oscillator 52 can rotate together with the shaft 4. The ultrasonic oscillator 52 has a rectangular shape or a circular shape in a plan view, and electrodes are formed on both surfaces of a piezoelectric material configured of lead zirconate titanate (PZT) by vapor deposition, printing or the like. Accordingly, in a state of facing the vascular wall, the ultrasonic waves can be emitted from the ultrasonic oscillator 52, and the reflected waves of the ultrasonic waves reflected at the vascular wall can be received. In other words, it is possible to transceive the ultrasonic waves. Through the transceiving, it is possible to capture the image of the vascular wall. The image is made by emitting the ultrasonic waves from the ultrasonic oscillator 52, and measuring a distance to the vascular wall from the time until the reflected waves once again return to the ultrasonic oscillator 52, thereby visualizing the state of the vascular wall.

In addition, from the ultrasonic oscillator 52, a plurality of signal lines (not illustrated) are inserted through the inside of the shaft 4 and are electrically connected to the connector portion 53.

The connector portion 53 is connected to the scanner apparatus 61 and can directly receive the rotating force from the scanner apparatus 61. The connector portion 53 is defined by a metal tubular body having conductivity such as copper. Accordingly, the connector portion 53 can be electrically connected to the scanner apparatus 61, and an image signal from the ultrasonic oscillator 52 can be transmitted to the display portion 64 through the scanner apparatus 61. Then, the image of the vascular wall is displayed on the display portion 64.

Next, the drive shaft insertion portion 210 will be described.

As illustrated in FIGS. 2 and 3, the drive shaft insertion portion 210 is defined by the resin medical tube according to the exemplary embodiment. In other words, as illustrated in FIGS. 2 and 3, the drive shaft insertion portion 210 has a resin first tube 7 having flexibility, a resin second tube 8 provided on a proximal side of the first tube 7 having the flexibility, and a resin third tube 9 provided on a proximal side of the second tube 8 having the flexibility.

The first tube 7 extends from a proximal to an intermediate portion on a distal side of the drive shaft insertion portion 210. In addition, the third tube 9 defines a portion of the distal side of the drive shaft insertion portion 210 and is fixed to a distal portion of the first tube 7. In this case, an inner peripheral surface of a proximal portion of the third tube 9 is fixed to an outer peripheral surface of the distal portion of the first tube 7.

In addition, the second tube 8 covers the distal portion of the first tube 7 and the proximal portion of the third tube 9. In other words, an inner peripheral surface of the second tube 8 is fixed to the outer peripheral surface of the distal portion of the first tube 7 and the outer peripheral surface of the proximal portion of the third tube 9.

The inner peripheral surface of the proximal portion of the third tube 9 is fixed to the outer peripheral surface of the distal portion of the first tube 7, and thus, it is possible to prevent kinks of the catheter main body 21. A fixing method of each of the portions is not particularly limited, and for example, adhesion using the adhesive agent, or fusion such as heat fusion and ultrasonic fusion can be used.

In the drive shaft insertion portion 210, from a proximal side toward the distal side, a first portion 11, a second portion 12, a third portion 13, and a fourth portion 14 are provided in this order. In addition, a fifth portion 15 is provided between the second portion 12 and the third portion 13.

The first portion 11 has a tubular resin layer 111. The resin layer 111 forms the first tube 7 within first portion 11.

The second portion 12 has a tubular inner layer 121 made from the resin, and a tubular outer layer 122 which is provided on an outer peripheral side of the inner layer 121 and made from the resin. In the illustrated configuration, the outer layer 122 covers an outer peripheral surface of the inner layer 121. Thus, the inner layer 121 forms the first tube 7, and the outer layer 122 forms the second tube 8 within the second portion 12.

The third portion 13 has a tubular inner layer 131 made from the resin, and a tubular outer layer 132 which is provided on an outer peripheral side of the inner layer 131 and made from the resin. In the illustrated configuration, the outer layer 132 covers an outer peripheral surface of the inner layer 131. The inner layer 131 forms the third tube 9, and the outer layer 132 forms the second tube 8 within the third portion 13.

The fourth portion 14 has a tubular resin layer 141. The resin layer 141 forms the third tube 9 within the fourth portion 14.

The fifth portion 15 has a tubular inner layer 151 made from the resin, an intermediate layer 153 which is provided on an outer peripheral side of the inner layer 151 and is made from the resin, and the tubular outer layer 122 which is provided on an outer peripheral side of the intermediate layer 153 and is made from the resin. In the illustrated configuration, the intermediate layer 153 covers an outer surface of the inner layer 151, and the outer layer 152 covers an outer peripheral surface of the intermediate layer 153. Note that, the inner layer 151 forms the first tube 7, and the intermediate layer 153 forms the third tube 9, and the outer layer 152 forms the second tube 8 within the fifth portion 15.

In addition, when flexural rigidity (rigidity) of the first portion 11 is G1, the flexural rigidity of the second portion 12 is G2, the flexural rigidity of the third portion 13 is G3, and the flexural rigidity of the fourth portion 14 is G4, the flexural rigidity of each portion has a relationship with each other portion based upon the following expression (1):

$$G1 > G2 > G3 > G4 \qquad (1)$$

Accordingly, it is possible to obtain the drive shaft insertion portion 210 which is excellent in pushability and the torque transmissibility which are forces to push the catheter 2 from the proximal side to the distal side to prevent the kinks.

The flexural rigidity of the fifth portion 15 is greater than the flexural rigidity G2 of the second portion 12, and less than the flexural rigidity G1 of the first portion 11. The fifth portion 15 may be disposed at another position, or may be omitted. In addition, in the drive shaft insertion portion 210, another portion or a plurality of other portions may be provided along the longitudinal direction.

In addition, in the drive shaft insertion portion 210, the resin layer 111 of the first portion 11, the inner layer 121 of the second portion 12, and the inner layer 151 of the fifth portion 15 are integrally formed of the same material. In other words, the first tube 7 is integrally formed of the same material. Accordingly, it is possible to improve the strength of the drive shaft insertion portion 210, and it is possible to prevent the kinks.

Further, the outer layer 122 of the second portion 12, the outer layer 132 of the third portion 13, and the outer layer 152 of the fifth portion 15 are integrally formed of the same material. In other words, the second tube 8 is integrally formed of the same material. Accordingly, it is possible to improve the strength of the drive shaft insertion portion 210, and it is possible to prevent the kinks.

Also, the inner layer 131 of the third portion 13, the resin layer 141 of the fourth portion 14, and the intermediate layer 153 of the fifth portion 15 are integrally formed of the same material. In other words, the third tube 9 is integrally formed of the same material. Accordingly, it is possible to improve the strength of the drive shaft insertion portion 210, and it is possible to prevent the kinks.

A thickness of the inner layer 121 and a thickness of the outer layer 122 of the second portion 12 are respectively thinner than a thickness of the resin layer 111 of the first portion 11. In addition, in the illustrated configuration, a thickness of the first portion 11, a thickness of the second portion 12, and a thickness of the third portion 13 are substantially the same as each other, and a thickness of the fourth portion 14 is the thinnest.

An inner diameter of the first portion 11, an inner diameter of the second portion 12, an inner diameter of the third portion 13, an inner diameter of the fourth portion 14, and an inner diameter of the fifth portion 15 are substantially the same as each other. In other words, the drive shaft insertion portion 210 has the constant inner diameter across the overall length thereof.

Accordingly, it is possible to achieve a reduced diameter in the drive shaft insertion portion 210.

Among an outer diameter of the first portion 11, an outer diameter of the second portion 12, an outer diameter of the third portion 13, an outer diameter of the fourth portion 14, and an outer diameter of the fifth portion 15, the outer diameter of the fourth portion 14 is the smallest.

In addition, the outer diameter of the first portion 11, the outer diameter of the second portion 12, and the outer diameter of the third portion 13 are substantially the same.

In addition, the flexural rigidity of the material of each portion has the following relationship with each other.

Firstly, the flexural rigidity of the material of the outer layer 122 of the second portion 12 is less than the flexural rigidity of the material of the resin layer 111 of the first portion 11. Then, since the thickness of the first portion 11 and the thickness of the second portion 12 are the same as each other, as aforementioned, the flexural rigidity of the second portion 12 is less than the flexural rigidity of the first portion 11.

In addition, the flexural rigidity of the material of the inner layer 131 of the third portion 13 is less than the flexural rigidity of the material of the inner layer 121 of the second portion 12, that is, the material of the resin layer 111 of the first portion 11, and less than the flexural rigidity of the configuration material of the outer layer 122 of the second portion 12. Accordingly, as aforementioned, the flexural rigidity of the third portion 13 is less than the flexural rigidity of the second portion 12.

Here, as the material of each portion, various resin materials having the desired flexibility can be employed respectively, as aforementioned. However, it is preferable the material contains the following resin materials, and particularly, it is preferable that each portion be made from the following resin materials.

Firstly, as the material of the resin layer 111 of the first portion 11, the inner layer 121 of the second portion 12, and the inner layer 151 of the fifth portion 15, the polyether ether ketone is preferable.

As the reason for this, the polyether ether ketone has comparatively greater flexural rigidity, and when blood coagulates, the coagulated blood is unlikely to adhere.

In addition, as the material of the outer layer 122 of the second portion 12, the outer layer 132 of the third portion 13, and the outer layer 152 of the fifth portion 15, for example, the polyolefin such as the polyethylene and the polypropylene is preferable, and particularly, the polyethylene is preferable.

As the reason for this, the polyolefin, particularly, the polyethylene has comparatively less flexural rigidity.

Note that, hereinafter, the material of the outer layer 122 of the second portion 12, the outer layer 132 of the third portion 13, and the outer layer 152 of the fifth portion 15 may be referred to as a "first material".

In addition, as the material of the inner layer 131 of the third portion 13, the resin layer 141 of the fourth portion 14, and the intermediate layer 153 of the fifth portion 15, for example, the polyolefin such as the polyethylene and the polypropylene is preferable, and particularly, the polyethylene is preferable.

As the reason for this, the polyolefin, particularly, the polyethylene has comparatively less flexural rigidity. In addition, when imaging the vascular wall through the drive shaft 3, the fourth portion 14 is a place where the ultrasonic oscillator 52 is positioned, and the polyolefin, particularly the polyethylene improves permeability of the ultrasonic waves.

Note that, hereinafter, the material of the inner layer 131 of the third portion 13, the resin layer 141 of the fourth portion 14, and the intermediate layer 153 of the fifth portion 15 may be referred to as a "second material".

In addition, it is preferable that a weight-average molecular weight (molecular weight) Mw2 of the second configuration material be smaller than a weight-average molecular weight (molecular weight) Mw1 of the first material. In other words, as the second material, it is preferable to employ the polyolefin which is the first material, particularly, the polyolefin of which the weight-average molecular weight is smaller than that of the polyethylene, particularly, the polyethylene. Accordingly, it is possible to cause the flexural rigidity of the second configuration material to be less than the flexural rigidity of the first material.

In addition, it is preferable that the density of the first material, for example, the polyolefin, particularly, the polyethylene be 0.94 g/cm$^3$ or above, and it is more preferable to be within a range of approximately 0.94 g/cm$^3$ to 0.96 g/cm$^3$.

In addition, it is preferable that the density of the second material, for example, the polyolefin, particularly, the polyethylene be within a range of approximately 0.91 g/cm$^3$ to 0.93 g/cm$^3$.

Here, as illustrated in FIG. 4, a proximal portion of the outer layer 122 of the second portion 12 adheres to the inner layer 121 of the second portion 12 or the resin layer 111 of the first portion 11 using the adhesive agent.

Specifically, a first adhesive agent 31 is provided at a bonding portion between the resin layer 111 and the outer layer 122, that is, between the resin layer 111 and the proximal surface of the outer layer 122. Between the inner layer 121 and the outer layer 122, in the vicinity of the bonding portion, a second adhesive agent 32 is provided.

As the first adhesive agent 31 and the second adhesive agent 32, without being particularly limited, it is preferable to employ a reaction system adhesive agent. As the reaction system adhesive agent, for example, it is possible to employ a radiation curing agent which is cured by radiation such as ultraviolet rays.

When causing the outer layer 122 to adhere to the inner layer 121 or the resin layer 111, the second adhesive agent 32 is first injected from a gap between the resin layer 111 and the proximal surface of the outer layer 122, thereby being cured.

It is preferable that a viscosity of the second adhesive agent 32 be comparatively low. Accordingly, the second adhesive agent 32 can be injected further to the distal side, and thus, it is possible to enhance the bonding strength between the outer layer 122 and the inner layer 121.

As a second adhesive agent 32, it is preferable to employ, for example, an acrylic resin-based adhesive agent and the like.

Next, the first adhesive agent 31 is injected into the gap between the resin layer 111 and the proximal surface of the outer layer 122 and cured, thereby sealing the gap.

It is preferable that the first adhesive agent 31 be comparatively high in viscosity and has resistance to chemicals. Accordingly, when the first adhesive agent 31 is injected into the gap, the first adhesive agent 31 is unlikely to flow to other portions from the gap, and thus, it is possible to reliably seal the gap. In addition, since a surface of the catheter main body 21 is processed by predetermined chemicals, it is possible to reliably prevent the chemicals from infiltrating into the gap during the processing.

As the first adhesive agent 31, it is preferable to employ, for example, an epoxy resin-based adhesive agent, a urethane resin-based adhesive agent or the like.

As described above, according to the catheter 2, softness gradually increases from the intermediate portion of the distal side of the drive shaft insertion portion 210 toward the distal direction, thereby being excellent in operability such as the pushability and the torque transmissibility, and it is possible to prevent the kinks and the like.

Hereinbefore, the medical tube and the catheter according to the disclosure herein have been described based on the illustrated exemplary embodiment. However, the disclosure is not limited thereto and the configuration of each portion can be replaced with an arbitrary configuration having a similar function. In addition, another arbitrary configuring element may be added to the disclosure.

In the disclosure here, the catheter main body is not limited to a component having a distal opening portion which is open at the distal thereof as a discharge port of a liquid. For example, the catheter main body may have a side hole passing through a side wall of the distal portion.

In addition, in the disclosure here, the image obtained through the catheter assembly, without being limited to the ultrasonic image, for example, may be an image which can be obtained optically, that is, an image which can be obtained by light-emitting and light-receiving. For example, the catheter may be a catheter which is employed in a diagnostic apparatus for an image by an optical signal, particularly, a diagnostic apparatus for an optical coherence tomography image (OCT), and the diagnostic apparatus for the optical frequency domain image utilizing wavelength sweeping (OFDI) which is an improved type of OCT. In this case, biological tissue is irradiated by near infrared rays emitted from the distal portion of the drive shaft, interference light is generated by causing reflected light from the biological tissue to interfere with reference light, and then, a cross-sectional image inside the biological lumen such as a blood vessel can be generated based on the interference light.

In addition, in the disclosure here, the inner layer and the outer layer of the second portion may be reversed. In other words, the inner layer 121 in the exemplary embodiment may become the outer layer, and the outer layer 122 may become the inner layer.

Still further, in the disclosure here, the inner layer and the outer layer of the third portion may be reversed. In other words, the inner layer 131 in the embodiment may become the outer layer, and the outer layer 132 may become the inner layer.

In addition, in the present invention, a sixth portion may be provided between the first portion and the second portion, and a seventh portion may be provided between the third portion and the fourth portion.

According to the exemplary embodiment of the disclosure, there is provided a resin medical tube including a first portion, a second portion, a third portion, and a fourth portion in this order from a proximal side toward a distal side.

The first portion has a tubular resin layer.

The second portion has a tubular inner layer and a tubular outer layer that is provided on an outer periphery side of the inner layer.

The third portion has the tubular inner layer and the tubular outer layer that is provided on the outer periphery side of the inner layer.

The fourth portion has the tubular resin layer.

When the rigidity of the first portion is G1, the rigidity of the second portion is G2, the rigidity of the third portion is G3, and the rigidity of the fourth portion is G4, the rigidity of each portion has a relationship with each of the other portions based upon the following expression (1):

$$G1>G2>G3>G4 \qquad (1)$$

According to the disclosure here, it is possible to provide the medical tube of which the rigidity is gradually decreased from an intermediate portion toward a distal side of the tube.

In addition, a catheter according to the disclosure here is inserted into a biological lumen to be used and includes a catheter main body having flexibility.

The catheter main body is characterized by having the medical tube according to the disclosure here.

The detailed description above describes a medical tube and catheter disclosed by way of example. The disclosure is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A resin medical tube comprising, in the following order from a proximal side toward a distal side:
   a first portion;
   a second portion;
   a third portion; and
   a fourth portion,
   wherein the first portion consists of only a single tubular resin layer,
   wherein the second portion consists of only a single tubular inner layer and a single tubular outer layer provided on an outer periphery side of the inner layer,
   wherein the third portion consists of only a single tubular inner layer and a single tubular outer layer provided on an outer periphery side of the inner layer,
   wherein the fourth portion consists of only a single tubular resin layer,
   wherein the single tubular resin layer of the first portion overlaps the single tubular resin layer of the fourth portion;
   wherein the resin layer of the first portion and the inner layer of the second portion are integrally formed of the same material;
   wherein the outer layer of the second portion and the outer layer of the third portion are integrally formed of the same material;
   wherein the resin layer of the fourth portion and the inner layer of the third portion are integrally formed of the same material; and
   wherein when the rigidity of the first portion is G1, the rigidity of the second portion is G2, the rigidity of the third portion is G3, and the rigidity of the fourth portion is G4, the rigidity of each portion having a relationship with each other potion based upon the following expression (1):

$$G1>G2>G3>G4 \quad (1).$$

2. The medical tube according to claim 1,
   wherein a thickness of the inner layer of the second portion is thinner than a thickness of the resin layer of the first portion.

3. The medical tube according to claim 1,
   wherein the rigidity of a material of the outer layer of the second portion is less than the rigidity of a material of the resin layer of the first portion.

4. The medical tube according to claim 1,
   wherein the rigidity of the material of the inner layer of the third portion is less than the rigidity of the material of the inner layer of the second portion.

5. The medical tube according to claim 1,
   wherein the rigidity of the material of the inner layer of the third portion is less than the rigidity of the material of the outer layer of the second portion.

6. The medical tube according to claim 1,
   wherein the material of the resin layer of the first portion contains a polyether ether ketone.

7. The medical tube according to claim 1,
   wherein the material of the outer layer of the second portion contains a polyolefin.

8. The medical tube according to claim 1,
   wherein the material of the inner layer of the third portion contains a polyolefin.

9. The medical tube according to claim 1,
   wherein the material of the outer layer of the second portion contains a polyolefin, and
   the material of the inner layer of the third portion contains a polyolefin of which a molecular weight is less than that of the polyolefin of the material of the outer layer of the second portion.

10. The medical tube according to claim 1,
    wherein an inner diameter of the first portion, an inner diameter of the second portion, an inner diameter of the third portion, and an inner diameter of the fourth portion are substantially the same as each other.

11. The medical tube according to claim 10,
    wherein an outer diameter of the fourth portion is the smallest among an outer diameter of the first portion, an outer diameter of the second portion, an outer diameter of the third portion, and the outer diameter of the fourth portion.

12. The medical tube according to claim 11,
    wherein the outer diameter of the first portion and the outer diameter of the second portion are substantially the same as each other.

13. The medical tube according to claim 1, further comprising:
    a first adhesive agent that is provided in a bonding portion between the resin layer of the first portion and the outer layer of the second portion; and
    a second adhesive agent that is provided between the inner layer of the second portion and the outer layer of the second portion.

14. The medical tube according to claim 13,
    wherein the first adhesive agent includes an epoxy resin-based adhesive agent or a urethane resin-based adhesive agent.

15. The medical tube according to claim 1, further comprising:
    a fifth portion that is provided between the second portion and the third portion.

16. The medical tube according to claim 15, wherein the fifth portion has a tubular inner layer, an intermediate layer provided on an outer peripheral side of the inner layer, and a tubular outer layer provided on an outer periphery side of the intermediate layer.

17. A catheter configured to be inserted into a biological lumen during use, the catheter comprising:
    a catheter main body; and
    a connector portion secured to a proximal portion of the catheter main body,
    wherein the catheter main body includes the medical tube according to claim 1.

* * * * *